US012268505B2

(12) United States Patent
Hong et al.

(10) Patent No.: US 12,268,505 B2
(45) Date of Patent: Apr. 8, 2025

(54) DEVICE FOR MEASURING BODILY FLUID DRAINAGE AMOUNT

(71) Applicant: KOREA UNIVERSITY RESEARCH AND BUSINESS FOUNDATION, Seoul (KR)

(72) Inventors: Kwang Dae Hong, Seoul (KR); Seung Joon Song, Seoul (KR); Sang Hoon Jung, Seoul (KR); Jae Young Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 403 days.

(21) Appl. No.: 17/762,631

(22) PCT Filed: Mar. 17, 2020

(86) PCT No.: PCT/KR2020/003616
§ 371 (c)(1),
(2) Date: Mar. 22, 2022

(87) PCT Pub. No.: WO2021/060635
PCT Pub. Date: Apr. 1, 2021

(65) Prior Publication Data
US 2022/0354402 A1    Nov. 10, 2022

(30) Foreign Application Priority Data
Sep. 23, 2019    (KR) ........................ 10-2019-0116718

(51) Int. Cl.
*A61B 5/20*    (2006.01)
(52) U.S. Cl.
CPC ....... *A61B 5/20* (2013.01); *A61M 2205/3389* (2013.01); *A61M 2205/3576* (2013.01)

(58) Field of Classification Search
CPC .. A61B 5/20; A61B 5/208; A61M 2205/3389; A61M 2205/3576
See application file for complete search history.

(56) References Cited

U.S. PATENT DOCUMENTS 3,838,691 A * 10/1974 Paludan ................ A61M 25/00
604/350
2010/0126268 A1 * 5/2010 Baily ..................... G01F 23/268
73/304 C (Continued)

FOREIGN PATENT DOCUMENTS

EP    1795875 A1 *  6/2007  ........... G01F 23/292
EP    1795875 B1 * 10/2008  ........... G01F 23/292

(Continued)

OTHER PUBLICATIONS

English Translation of International Search Report in PCT/KR2020/003616, mailed Jul. 1, 2020, 2 pages.

*Primary Examiner* — Catharine L Anderson
*Assistant Examiner* — Jihad Dakkak
(74) *Attorney, Agent, or Firm* — Meunier Carlin & Curfman LLC

(57) ABSTRACT

The present invention relates to a device for measuring a bodily fluid drainage amount, the device comprising: a measurement case which is formed of a rigid material and provided with a bodily fluid measurement space therein; a drainage tube which is coupled to an entrance of the measurement case in a releasable structure and transfers bodily fluids discharged from a human body to the bodily fluid measurement space of the measurement case; a plurality of fluid level sensors, which are horizontally disposed on an upper surface of the measurement case and measure and inform fluid levels of the bodily fluids collected in the bodily fluid measurement space; and a control device which receives and analyzes the fluid levels of the bodily fluids, (Continued)

infers a tilt of the measurement case from a difference in the fluid levels of the bodily fluids, and calculates and informs a bodily fluid drainage amount.

12 Claims, 3 Drawing Sheets

(56) References Cited

U.S. PATENT DOCUMENTS

| | | | | |
|---|---|---|---|---|
| 2011/0166537 A1* | 7/2011 | Paulen | ............... | A61B 5/208 604/318 |
| 2015/0362351 A1* | 12/2015 | Joshi | ............... | G01F 15/003 700/282 |
| 2017/0021068 A1* | 1/2017 | Gaskin | ............... | A61M 1/06 |
| 2018/0360365 A1* | 12/2018 | Yadav | ............... | A61B 5/1032 |
| 2020/0016306 A1* | 1/2020 | Weber | ............... | A61M 1/064 |

FOREIGN PATENT DOCUMENTS

| | | | | |
|---|---|---|---|---|
| JP | 5671017 B2 | 2/2015 | | |
| KR | 1010163710000 B | 2/2011 | | |
| KR | 1020110104969 A | 9/2011 | | |
| KR | 1020180036022 A | 4/2018 | | |
| KR | 1020190061140 A | 6/2019 | | |
| WO | WO-2008119993 A1 * | 10/2008 | ......... | A61M 1/0001 |

\* cited by examiner d11 = d21)
d12 = d22)

DEVICE FOR MEASURING BODILY FLUID DRAINAGE AMOUNT

CROSS REFERENCE TO RELATED APPLICATIONS

This application is a United States National Phase Patent Application of International Patent Application Number PCT/KR2020/003616, filed on Mar. 17, 2020, which claims the benefit of priority to Korean Provisional Application No. 10-2019-0116718, filed Sep. 23, 2019, which is incorporated by reference herein in its entirety.

TECHNICAL FIELD

The following description relates to a device for measuring a bodily fluid drainage amount, and more particularly, to a device for measuring a bodily fluid drainage amount so as to automatically, more easily and accurately measure the bodily fluid drainage amount.

BACKGROUND ART

The body fluid amount of a patient needs to be monitored in an operating room, medically ill/surgical intensive care units, and before and after major surgical operation, which may require prolonged anesthesia or may cause a hemodynamic instable situation.

For example, after instructing the patient to fast before the operation, a medical staff compares the total amount of water injected into the patient with the amount of water excreted in the urine to perform the operation when the two amounts of water match each other.

Accordingly, in the related art, as illustrated in FIG. 1, a foley catheter 1 is mounted in the bladder through the urethra to a patient who needs intensive monitoring of the body fluid amount and connected to the outside of the body, and a urine collector 2 implemented of a vinyl material measures the urine drainage amount.

However, in the device for measuring the urine drainage amount, a nurse manually repeats every hour an operation of measuring the amount of urine accumulated in the urine collector and turning a lever to flush the urine into a collection container. This operation occupies a significant portion of the nurse's work and may be inaccurate if a measurement time is not properly observed, and for the patient, it may be difficult to get a sound sleep due to the nurse's treatment every hour.

In addition, since the urine collector 2 is formed of a vinyl material with a scale drawn thereon, it is inconvenient to perform an operation of measuring an accurate urine drainage amount only after the urine collector 2 is erected in a vertical direction.

DISCLOSURE OF THE INVENTION

Technical Goals

To solve the above problems, an aspect provides a device for measuring a bodily fluid drainage amount so as to measure and inform an accurate bodily fluid drainage amount at all times even if the device is tilted in various directions according to a patient's posture.

Another aspect provides a device for measuring a bodily fluid drainage amount so as to automatically measure and discharge the bodily fluid drainage amount per unit time.

Aspects of the present disclosure are not limited to the aforementioned aspects, and other unmentioned aspects will be clearly understood by those skilled in the art from the following description.

Technical Solutions

As a means for solving the above problems, according to an aspect, there is provided a device for measuring a bodily fluid drainage amount including a measurement case which is formed of a rigid material and provided with a bodily fluid measurement space therein; a drainage tube which is coupled to an entrance of the measurement case in a releasable structure and transfers bodily fluids discharged from a human body to the bodily fluid measurement space of the measurement case; a plurality of fluid level sensors, which are horizontally disposed on an upper surface of the measurement case and measure and inform fluid levels of the bodily fluids collected in the bodily fluid measurement space; and a control device which receives and analyzes the fluid levels of the bodily fluids, infers a tilt of the measurement case from a difference in the fluid levels of the bodily fluids, and by taking the tilt of the measurement case and the fluid levels of the bodily fluids into consideration together, calculates and informs a bodily fluid drainage amount.

The control device may perform an operation of measuring the fluid levels of the bodily fluids by activating operatively the plurality of fluid level sensors at a predetermined period.

The device for measuring the bodily fluid drainage amount may further include an entrance valve to close the entrance of the measurement case while the plurality of fluid level sensors is operatively activated under the control of the control device.

Further, the device for measuring the bodily fluid drainage amount may further include a collection container which is coupled to an exit of the measurement case in a releasable structure to temporarily collect the bodily fluids discharged through the exit of the measurement case; and an exit valve of opening the exit of the measurement case at a predetermined period under the control of the control device.

The control device may further include a function of forcibly opening the exit valve when the bodily fluid drainage amount is equal to or greater than a predetermined value.

Further, the control device may further include a function of forcibly closing the entrance valve while the bodily fluids are discharged through the exit of the measurement case.

The device for measuring the bodily fluid drainage amount may further include an image sensor to measure colors of the bodily fluids, in which the control device may confirm and inform the occurrence of abnormal symptoms based on the colors of the bodily fluids of the image sensor.

In addition, at least one of the control device, the plurality of fluid level sensors, the entrance valve, and the exit valve may communicate in an IoT communication method, and the control device may further include a function of providing measurement results of the bodily fluid drainage amount to a predetermined external device.

Advantageous Effects

According to the present disclosure, a measurement case that collects and measures bodily fluids is formed of a rigid material and then a plurality of sensors is distributed in the measurement case, thereby calculating and informing the same bodily fluid drainage amount at all times even if the device is tilted in various angles according to a patient's posture. Accordingly, the patient may freely take a desired posture regardless of the operation of measuring the bodily fluid drainage amount.

In addition, the bodily fluid drainage amount per unit time may be automatically measured and discharged so that manual intervention of a third party is not required, and as a result, the work intensity of medical staffs related to the operation of measuring the bodily fluid drainage amount may be minimized.

In addition, it is possible to make device installation and use more convenient using IoT communication technology, and if necessary, to provide measurement results even to external devices such as medical staff terminals, guardian terminals, and medical institution servers.

BEST MODE FOR CARRYING OUT THE INVENTION

Figure 1:
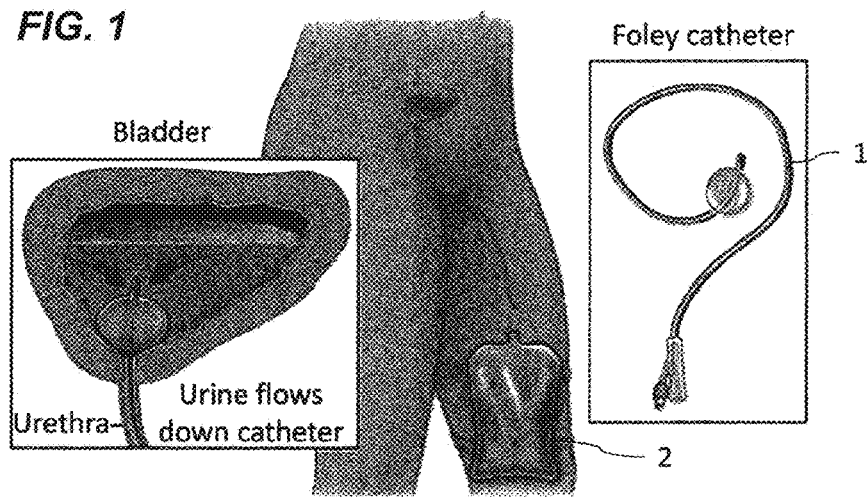
FIG. 1 is a diagram illustrating a device for measuring a urine amount according to the related art.

The following contents illustrate only a principle of the present disclosure. Therefore, those skilled in the art may implement the principle of the present disclosure and invent various devices included in the concept and scope of the present disclosure although not clearly described or illustrated in the present specification. In addition, it is to be understood that all conditional terms and embodiments mentioned in the present specification are obviously intended only to understand a concept of the present disclosure in principle, and the present disclosure is not limited to embodiments and states particularly mentioned as such.

Further, it is to be understood that all detailed descriptions mentioning specific embodiments of the present disclosure as well as principles, aspects, and embodiments of the present disclosure are intended to include structural and functional equivalences thereof. Further, it is to be understood that these equivalences include an equivalence that will be developed in the future as well as an equivalence that is currently well-known, that is, all elements invented so as to perform the same function regardless of a structure.

Accordingly, for example, it should be understood that the block diagram herein represents conceptual views of exemplary circuits embodying the principle of the present disclosure. Similarly, it is to be understood that all flow charts, state transition diagrams, pseudo-codes, and the like, illustrate various processes that may be tangibly embodied in a computer readable medium and that are executed by computers or processors regardless of whether or not the computers or the processors are clearly illustrated.

Functions of various elements including processors or functional blocks represented as concepts similar to the processors and illustrated in the accompanying drawings may be provided using hardware having capability to execute software in association with appropriate software as well as dedicated hardware. When the functions are provided by the processors, they may be provided by a single dedicated processor, a single shared processor, or a plurality of individual processors, and some of them may be shared with each other.

Further, the explicit use of terms such as processor, control, or similar concepts should not be interpreted exclusively as hardware capable of executing software, and may implicitly include, without limitation, digital signal processor (DSP) hardware, a ROM, a RAM, and a non-volatile memory for storing the software. Other well-known hardware may also be included.

In the appended claims of the present specification, the components represented as means for performing the functions described in the detailed description are intended to include all methods that perform functions including all types of software, including, for example, a combination of circuit elements performing the function or firmware/microcode, etc. and is coupled with an appropriate circuit for executing the software so as to perform the functions. It is to be understood that the present disclosure as defined by the appended claims encompasses any means capable of providing a function, as the functions provided by the various listed means are combined and combined with the manner in which the claims require.

The above-mentioned objects, features, and advantages will become more obvious from the following detailed description associated with the accompanying drawings. Therefore, those skilled in the art to which the present disclosure pertains may easily practice a technical idea of the present disclosure. Further, in describing the present disclosure, when it is decided that a detailed description of a well-known technology associated with the present disclosure may unnecessarily make the gist of the present disclosure unclear, the detailed description will be omitted.

Figure 2:
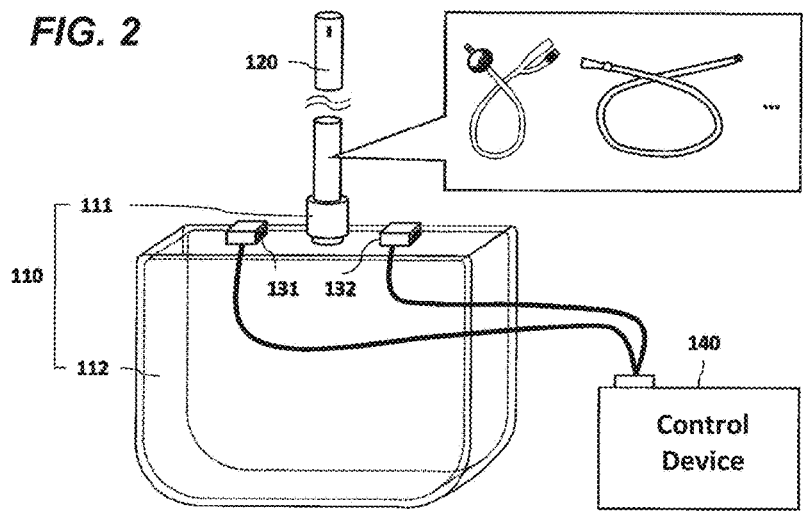
FIGS. 2 and 3 are diagrams for describing a device for measuring a bodily fluid drainage amount according to a first embodiment of the present disclosure.
Figure 3:
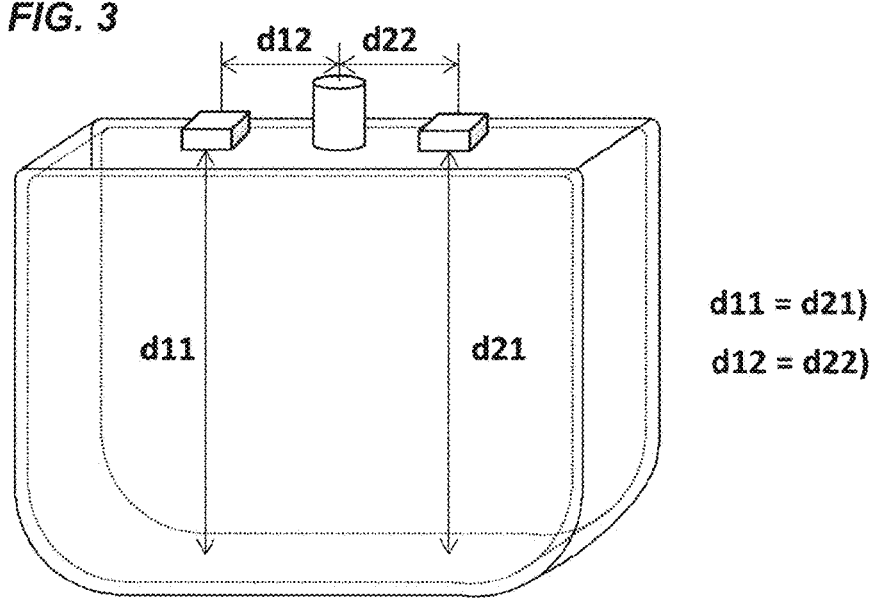

FIG. 2 is a diagram for describing a device for measuring a bodily fluid drainage amount according to a first embodiment of the present disclosure.

Referring to FIG. 2, a device 100 for measuring a bodily fluid drainage amount of the present disclosure is configured by including a measurement case 110, a drainage tube 120, a plurality of fluid level sensors 131 and 132, a control device 140, and the like.

The measurement case 110 is formed of a rigid material to maintain a predetermined shape. In addition, a bodily fluid measurement space 111 provided therein and an entrance 112 connected with a bodily fluid collection space are provided.

The drainage tube 120 is coupled to the entrance of the measurement case in a releasable structure, and transfers bodily fluids discharged from a human body to the bodily fluid measurement space 111 of the measurement case 110.

For reference, the present disclosure may measure drainage amounts of all bodily fluids in the human body, such as gastric contents, bile, and ascites as well as the urine. Accordingly, the drainage tube of the present disclosure may be implemented in various types, such as a urinary catheter into which the bladder is inserted, a nasogastric intubation inserted into the stomach through the nose and esophagus, a bile drainage tube inserted into the liver through the skin, and an ascites drainage tube inserted into the abdomen through the skin.

The plurality of fluid level sensors 131 and 132 are horizontally disposed on an upper surface of the measurement case 110 to measure and inform the fluid levels of the bodily fluids collected in the bodily fluid measurement space, respectively. The fluid level sensors 131 and 132 may be implemented by vertically irradiating a laser or ultrasonic waves and then receiving and analyzing reflected waves thereof to measure the fluid levels of the bodily fluids, but may be variously changed by the implementation method as needed.

In this case, the fluid level sensors 131 and 132 are preferably disposed to be symmetrical to each other with respect to a center point of the upper surface of the measurement case. That is, the fluid level sensors 131 and 132 are disposed to have the same vertical distance (d11=d21) from the bottom of the measurement case and the same horizontal distance (d12=d22) from the entrance of the measurement case.

The control device 140 acquires and stores in advance information on a correlation between an average fluid level of the bodily fluids and a bodily fluid drainage amount. In addition, all of the fluid levels of the bodily fluids values at multiple points measured by the plurality of fluid level sensors 131 and 132 are summed up and then averaged to calculate an average fluid level of the bodily fluids, and the calculated average fluid level of the bodily fluids is converted and output to the bodily fluid drainage amount according to a correlation between a predetermined fluid level of the bodily fluids and a bodily fluid drainage amount.

Figure 4:
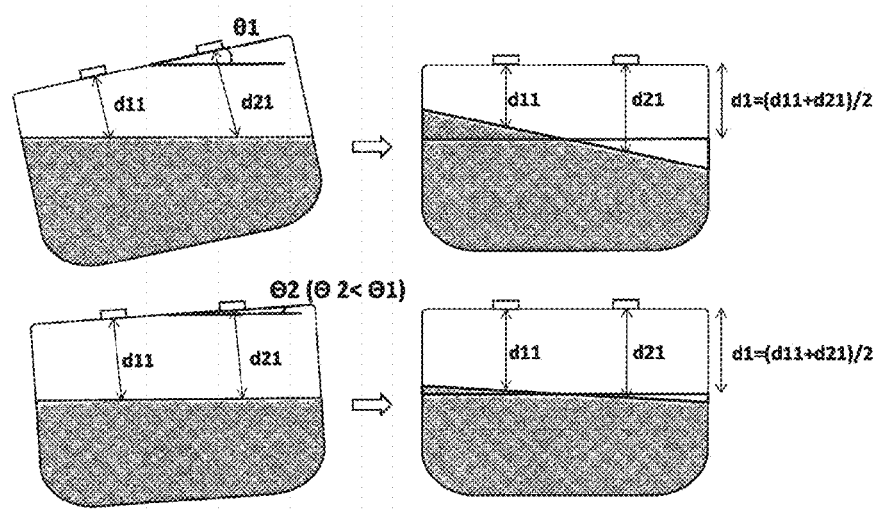
FIG. 4 is a diagram illustrating a difference in fluid levels of bodily fluids according to a tilt of a measurement case.

FIG. 4 is a diagram illustrating a difference in fluid levels of bodily fluids according to a tilt of the measurement case.

Referring to FIG. 4, it may be seen that a difference in the fluid levels of the bodily fluids linearly increases in proportion to the tilt of the measurement case. In addition, when all the fluid level values d11 and d21 of the bodily fluids at multiple points are summed up and averaged (d1=(d11+d21)/2), it may be seen that the value d1 is the same as the bodily fluid level value when the same bodily fluid drainage amount is measured after erecting the measurement case.

However, the bodily fluid drainage amount corresponding to each of the bodily fluid level values while the measurement case is erected may be variously changed according to the shape, size, and the like of the bodily fluid measurement space 111.

Accordingly, in the present disclosure, as described above, after information on the correlation between the average fluid level of the bodily fluids and the bodily fluid drainage amount is acquired and stored in advance, the bodily fluid drainage amount corresponding to the average fluid level of the bodily fluids may be finally calculated based on the information.

That is, according to the present disclosure, it is possible to calculate and inform an accurate bodily fluid drainage amount at all times regardless of various tilts of the measurement case, thereby automatically performing an operation of measuring the bodily fluid drainage amount without separate intervention of medical staffs or guardians.

Figure 5:
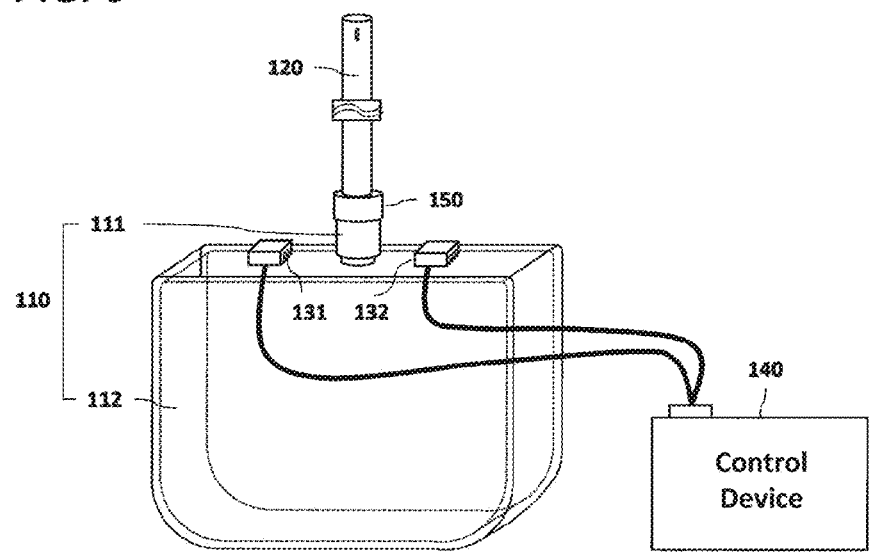
FIG. 5 is a diagram for describing a device for measuring a bodily fluid drainage amount according to a second embodiment of the present disclosure.

FIG. 5 is a diagram for describing a device for measuring a bodily fluid drainage amount according to a second embodiment of the present disclosure.

Referring to FIG. 5, the device 100 for measuring the bodily fluid drainage amount of the present disclosure further includes an entrance valve 150 for closing or opening the entrance of the measurement case, in addition to the measurement case 110, the drainage tube 120, the plurality of fluid level sensors 131 and 132, and the control device 140.

In addition, the control device 140 activates operatively the plurality of fluid level sensors 131 and 132 at a predetermined period (e.g., 1 hour, 8 hours, and 24 hours) to perform the operation of measuring the fluid levels of the bodily fluids. In addition, while the operation of measuring the fluid levels of the bodily fluids is performed, the entrance of the measurement case is closed through the entrance valve 150 to temporarily block the inflow of a new bodily fluid.

Figure 6:
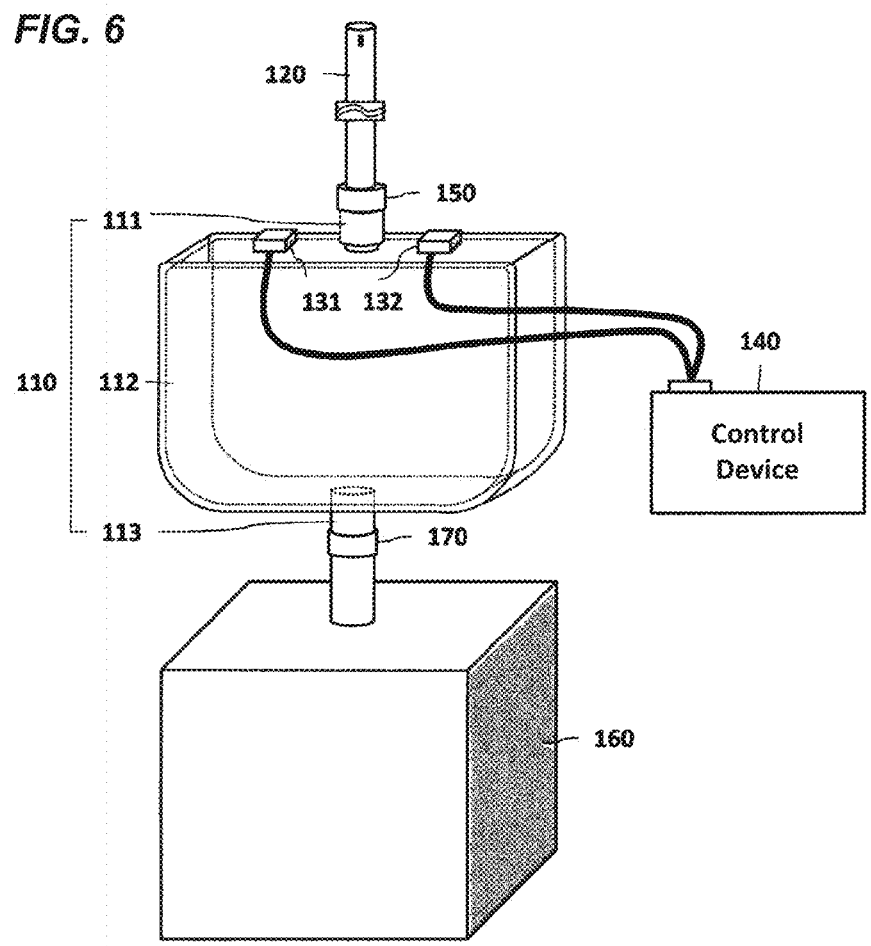
FIG. 6 is a diagram for describing a device for measuring a bodily fluid drainage amount according to a third embodiment of the present disclosure.

FIG. 6 is a diagram for describing a device for measuring a bodily fluid drainage amount according to a third embodiment of the present disclosure.

Referring to FIG. 6, the measurement case 110 of the present disclosure may further include an exit 113 as well as the entrance 111.

In addition, in addition to the drainage tube 120, the plurality of fluid level sensors 131 and 132, the control device 140, and the entrance valve 150, the device may further include a collection container 160 which is coupled to the exit 113 of the measurement case 110 in a releasable structure to temporarily collect the bodily fluids discharged through the exit of the measurement case, and an exit valve 170 of opening the exit 113 of the measurement case 110 at a predetermined period under a control of the control device 140.

In addition, the control device 140 closes the entrance valve 150 while discharging the bodily fluids collected in the measurement case 110, thereby preventing a possibility to discharge a newly introduced bodily fluid immediately without a measurement process in advance.

As such, according to the present disclosure, the bodily fluid drainage amount is repeatedly measured in a predetermined time unit through the measurement case 110, but the measured bodily fluids may be discharged to a separate device such as the collection container 160.

As a result, it is possible to automatically perform the operation of measuring the bodily fluid drainage amount without separate intervention of medical staffs or guardians, and simultaneously to minimize the efforts required to manage and maintain the device.

In addition, in the description, only the case where one drainage tube 120 is coupled to the measurement case 110 has been described, but if necessary, it will be natural that a plurality of drainage tubes 120 may be simultaneously coupled to each other.

Figure 7:
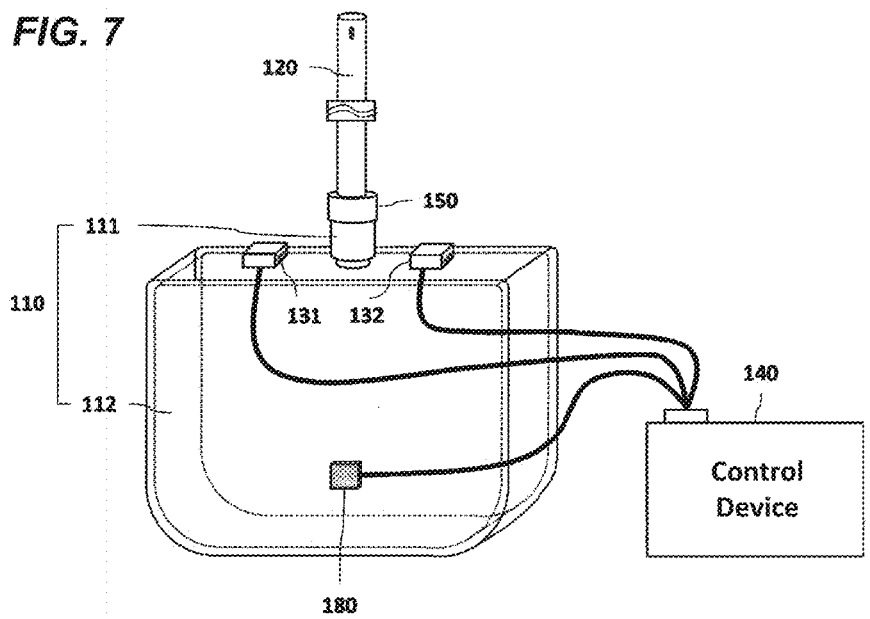
FIG. 7 is a diagram for describing a device for measuring a bodily fluid drainage amount according to a fourth embodiment of the present disclosure.

FIG. 7 is a diagram for describing a device for measuring a bodily fluid drainage amount according to a fourth embodiment of the present disclosure.

The measurement case 110 of FIG. 7 further includes an image sensor 180 for sensing and informing the colors of the bodily fluids, and at this time, the control device 140 pre-stores color information corresponding to abnormal symptoms and analyzes the colors of the bodily fluids of the image sensor 180 based thereon to confirm and inform the occurrence of the abnormal symptoms.

For example, when color information corresponding to a hematuria condition is stored in advance and the image sensor 180 senses the color of the bodily fluid corresponding to the color information, an alarm signal for informing occurrence of an abnormal symptom is immediately generated and output. In other words, it is possible to monitor a patient's condition based on the colors of the bodily fluids and automatically inform the monitored patient's condition to the medical staffs.

In addition, at least one of the control device 140, the plurality of fluid level sensors 131 and 132, the entrance valve 150, and the exit valve 170 of the present disclosure additionally includes an IoT communication module to transmit and receive various signals based on IoT communication.

In particular, the control device 140 communicates with an external device such as a medical staff terminal, a guardian terminal, and a medical institution server, through the IoT communication module, and may also inform a current bodily fluid drainage amount to the external device in real time.

The method according to the present disclosure described above may be prepared with a program to be executed on a computer and stored in a computer-readable recording medium, and examples of the computer-readable recording medium include a ROM, a RAM, a CD-ROM, a magnetic tape, a floppy disk, an optical data storage device, etc., and also include media to be implemented in the form of a carrier wave (for example, transmission through Internet).

The computer readable recording media may be stored and executed with codes which may be distributed in the computer system connected through a network and read by a computer in a distribution method. In addition, functional programs, codes, and code segments for implementing the method may be easily inferred by programmers in the art to which the present disclosure pertains.

While the preferred embodiments of the present disclosure have been illustrated and described above, the present disclosure is not limited to the aforementioned specific embodiments, various modifications may be made by a person with ordinary skill in the technical field to which the present disclosure pertains without departing from the subject matters of the present disclosure that are claimed in the appended claims, and these modifications should not be appreciated individually from the technical spirit or prospect of the present disclosure.

The invention claimed is:

1. A device for measuring a bodily fluid drainage amount, the device comprising:
   a measurement case which is formed of a rigid material and provided with a bodily fluid measurement space therein;
   a drainage tube which is coupled to an entrance of the measurement case in a releasable structure and transfers bodily fluids discharged from a human body to the bodily fluid measurement space of the measurement case;
   a plurality of fluid level sensors horizontally disposed on an upper surface of the measurement case and spaced equidistant from a center point of the upper surface, wherein the plurality of fluid level sensors measure and inform fluid levels of the bodily fluids collected in the bodily fluid measurement space,
   wherein each of the plurality of fluid level sensors measures a distance between the respective fluid level sensor and the bodily fluid in a direction normal to the respective fluid sensor; and
   a control device which receives and analyzes the fluid levels of the bodily fluids, infers a tilt of the measurement case from a difference in the fluid levels of the bodily fluids, and by taking the tilt of the measurement case and the fluid levels of the bodily fluids into consideration together, calculates and informs a bodily fluid drainage amount.

2. The device of claim 1, wherein the control device performs an operation of measuring the fluid levels of the bodily fluids by activating operatively the plurality of fluid level sensors at a predetermined period.

3. The device of claim 2, further comprising:
   an entrance valve to close the entrance of the measurement case while the plurality of fluid level sensors is operatively activated under a control of the control device.

4. The device of claim 3, further comprising:
   a collection container which is coupled to an exit of the measurement case in a releasable structure to temporarily collect the bodily fluids discharged through the exit of the measurement case; and
   an exit valve of opening the exit of the measurement case at a predetermined period under the control of the control device.

5. The device of claim 4, wherein the control device further comprises a function of forcibly opening the exit valve when the bodily fluid drainage amount is equal to or greater than a predetermined value.

6. The device of claim 4, wherein the control device further comprises a function of forcibly closing the entrance valve while the bodily fluids are discharged through the exit of the measurement case.

7. The device of claim 4, further comprising:
   an image sensor to measure colors of the bodily fluids,
   wherein the control device confirms and informs the occurrence of abnormal symptoms based on the colors of the bodily fluids of the image sensor.

8. The device of claim 4, wherein at least one of the control device, the plurality of fluid level sensors, the entrance valve, and the exit valve communicates in an IoT communication method.

9. The device of claim 8, wherein the control device further comprises a function of providing measurement results of the bodily fluid drainage amount to a predetermined external device.

10. The device of claim 1, wherein the plurality of fluid level sensors comprises a first fluid level sensor and a second fluid level sensor,
    wherein the first fluid level sensor determines a first fluid level by measuring a distance between the first fluid level sensor and the bodily fluid in a direction normal to the first fluid level sensor, and
    wherein the second fluid level sensor determines a second fluid level by measuring a distance between the second fluid level sensor and the bodily fluid in a direction normal to the second fluid level sensor.

11. The device of claim 10, wherein the control device is configured to determine an average fluid level of the bodily fluids by receiving the first fluid level and the second fluid level and calculating an arithmetic mean of the first fluid level and the second fluid level.

12. The device of claim 1, wherein the plurality of fluid level sensors are configured to irradiate a laser or transmit ultrasonic waves in a vertical direction toward the bodily fluid.

* * * * *